United States Patent [19]

Kugel

[11] 4,382,699

[45] May 10, 1983

[54] LABORATORY METHOD FOR TESTING THE EFFECTIVENESS OF RELEASE AGENTS FOR PREVENTING COAL FROM FREEZING TO THE SIDES OF COAL CARS

[75] Inventor: Roger W. Kugel, Winona, Minn.

[73] Assignee: Nalco Chemical Company, Oak Brook, Ill.

[21] Appl. No.: 325,696

[22] Filed: Nov. 30, 1981

[51] Int. Cl.$^3$ .................... G01N 33/00; G01N 17/00; G01N 21/00

[52] U.S. Cl. ........................................ 374/46; 374/51; 201/1; 73/150 A; 436/2

[58] Field of Search ............. 436/2; 73/150 A; 201/1; 374/41, 45, 46, 51, 55, 50

[56] References Cited

U.S. PATENT DOCUMENTS

| | | | |
|---|---|---|---|
| 2,402,738 | 6/1946 | Dietert | 374/55 |
| 3,718,035 | 2/1973 | Doerr | 374/50 |
| 4,092,843 | 6/1978 | Matskevich et al. | 374/51 |

*Primary Examiner*—Michael S. Marcus
*Attorney, Agent, or Firm*—John G. Premo; Robert A. Miller

[57] ABSTRACT

A method of testing additives for the ability to prevent coal particles from freezing and adhering to the sides of coal cars and metal storage devices which comprises the steps of:

(a) coating the treatment to be tested on the inside of a small interior diameter steel or aluminum cylinder;
(b) soaking the thus-treated cylinder in water for a short time to simulate exposure to precipitation;
(c) immediately loading the water-treated cylinder with coal particles;
(d) compressing the coal within the cylinder;
(e) freezing the coal within the cylinder;
(f) removing the coal from the cylinder using means capable of measuring the force required to remove the coal; and
(g) comparing that force against the force required to remove the coal from a similar non-treated cylinder.

1 Claim, No Drawings

LABORATORY METHOD FOR TESTING THE EFFECTIVENESS OF RELEASE AGENTS FOR PREVENTING COAL FROM FREEZING TO THE SIDES OF COAL CARS

INTRODUCTION

In freezing weather, finely divided coal will oftentimes stick to the sides of coal cars and is very difficult to remove. Additives have been developed which, when sprayed upon the sides of the coal cars, promote the ready release of coal particles therefrom.

It is expensive and oftentimes difficult to evaluate coal car side release agents by coating actual cars in cold weather. If a simple test for evaluating coal car side freeze release agents were available, a valuable contribution to the art would be made.

THE INVENTION

A method of testing additives for the ability to prevent coal particles from freezing and adhering to the sides of coal cars and metal storage devices which comprises the steps of:

(a) coating the treatment to be tested on the inside of a small interior diameter steel or aluminum cylinder;

(b) soaking the thus-treated cylinder in water for a short time to simulate exposure to precipitation;

(c) immediately loading the water-treated cylinder with coal particles;

(d) compressing the coal within the cylinder;

(e) freezing the coal within the cylinder;

(f) removing the coal from the cylinder using means capable of measuring the force required to remove the coal; and (g) comparing that force against the force required to remove the coal from a similar non-treated cylinder.

Steel or aluminum cylinders ($2\frac{1}{2}''$ ID $\times 3\frac{3}{4}''$ L) are used for the side release tests. The chemical treatment may be applied to the inside surfaces of the cylinders by spraying on or wiping on with a towel. The cylinders are then presoaked in $H_2O$ for one minute to simulate exposure to precipitation, and immediately loaded with coal. The coal in each cylinder is compressed to a constant value (3–9 psi), and the cylinders are placed in the freezer for a set period of time. Typically the cylinders are frozen overnight at $-25°$ C. ($-15°$ F.). After freezing, a piston arrangement is used on the Soiltest Model U164 Compression Strength Tester to force the frozen coal out of the metal cylinders. The force required to remove the coal from the cylinders is directly related to the shear strength at the frozen coal-metal interface. A good side release agent reduces this shear strength by more than 50%.

It is understood that variations may be made. As an example, while the dimensions for the steel or aluminum cylinder have been shown as being $2\frac{1}{2}''$ ID, it may be of a smaller or larger dimension. Specifically, the inside diameter of the test cylinder should not be less than five times the diameter of the largest particles contained in the sample. For example, Applicant tested materials having particle diameters $-\frac{1}{2}''$ so Applicant's cylinder diameter was $2\frac{1}{2}''$. This ratio between the material top-size and the smallest dimension of the test cell of 1:5 has been adopted by the Standards Committee at the National Coal Conference and Workshop.

Similarly, this cylinder may be longer or shorter. In any event, it should not be more than 1' or so due to ease of handling in the laboratory.

Having thus described my invention, it is claimed as follows:

1. A method of testing additives for the ability to prevent coal particles from freezing and adhering to the sides of coal cars and metal storage devices which comprises the steps of:

(a) coating a chemical treatment to be tested on the inside of a small interior diameter steel or aluminum cylinder; (b) soaking the thus-treated cylinder in water for a short time to simulate exposure to precipitation;

(c) immediately loading the water-treated cylinder with coal particles;

(d) compressing the coal within the cylinder;

(e) freezing the coal within the cylinder;

(f) removing the coal from the cylinder using means capable of measuring the force required to remove the coal; and (g) comparing that force against the force required to remove the coal from a similar non-treated cylinder.

* * * * *